(12) United States Patent
Klein et al.

(10) Patent No.: US 10,907,676 B2
(45) Date of Patent: Feb. 2, 2021

(54) SPRING FOR CONNECTING A PIPE TO A CONNECTOR

(71) Applicant: LIL MONKEY LTD., Shoham (IL)

(72) Inventors: Ido Klein, Shoham (IL); Alon Lavi, Shoham (IL)

(73) Assignee: LIL MONKEY LTD., Shoham (IL)

( * ) Notice: Subject to any disclaimer, the term of this patent is extended or adjusted under 35 U.S.C. 154(b) by 203 days.

(21) Appl. No.: 15/546,347

(22) PCT Filed: Jan. 28, 2016

(86) PCT No.: PCT/IL2016/050097
§ 371 (c)(1),
(2) Date: Jul. 26, 2017

(87) PCT Pub. No.: WO2016/120878
PCT Pub. Date: Aug. 4, 2016

(65) Prior Publication Data
US 2018/0023609 A1  Jan. 25, 2018

Related U.S. Application Data

(60) Provisional application No. 62/109,202, filed on Jan. 29, 2015.

(51) Int. Cl.
*F16B 21/09* (2006.01)
*C12M 1/12* (2006.01)
(Continued)

(52) U.S. Cl.
CPC ............. *F16B 21/09* (2013.01); *C12M 25/00* (2013.01); *F16B 7/042* (2013.01); *E04H 15/32* (2013.01); *E04H 15/44* (2013.01); *F16L 37/086* (2013.01)

(58) Field of Classification Search
CPC ...... F16B 21/086; F16B 21/082; F16B 21/08; F16B 21/065; F16B 21/06; F16B 12/26;
(Continued)

(56) References Cited

U.S. PATENT DOCUMENTS 2,546,387 A * 3/1951 Coffing .................. F16B 7/042
16/427
2,620,210 A  12/1952 Heinrich
(Continued)

FOREIGN PATENT DOCUMENTS

DE      324046 C  *  8/1920  ............. F16B 7/105
DE   2024508 A1  * 12/1971  ............. F16B 7/042
(Continued)

*Primary Examiner* — Daniel J Wiley
(74) *Attorney, Agent, or Firm* — The Roy Gross Law Firm, LLC; Roy Gross

(57) ABSTRACT

A spring for connecting a pipe to a rod, the spring including a flat tab attached to a rod and aligned with a first face of the rod and a second unattached tab aligned with a second face of the rod that is opposite to the first face, and a diagonal bridge connecting the first flat tab and the second unattached tab, wherein the angle between the attached tab and the diagonal bridge is greater than 90° and a button located on the flat tab, wherein the button protrudes from a distal end of the rod when the spring is normally open, and wherein the button is configured to engage with a corresponding hole in a pipe.

12 Claims, 6 Drawing Sheets

(51) Int. Cl.
*F16B 7/04* (2006.01)
*E04H 15/32* (2006.01)
*E04H 15/44* (2006.01)
*F16L 37/086* (2006.01)

(58) Field of Classification Search
CPC .......... F16B 12/40; F16B 7/105; F16B 7/042; Y10T 403/32483; Y10T 403/32524; Y10T 403/606; Y10T 403/32459; Y10T 403/7077
See application file for complete search history.

(56) References Cited

U.S. PATENT DOCUMENTS

| | | | | |
|---|---|---|---|---|
| 2,950,134 | A * | 8/1960 | Strange | F16B 21/086 403/329 |
| 2,992,845 | A * | 7/1961 | Blanchard | E04H 15/60 248/188.5 |
| 3,712,652 | A | 1/1973 | Uilkema | |
| 4,085,763 | A * | 4/1978 | Thomas | A45B 7/00 135/69 |
| 4,247,216 | A | 1/1981 | Pansini | |
| 4,431,331 | A | 2/1984 | Brody | |
| 4,528,998 | A | 7/1985 | Gamm | |
| 5,143,476 | A * | 9/1992 | Pruis | F16B 7/042 403/108 |
| 5,144,780 | A | 9/1992 | Gieling | E04B 1/5831 135/114 |
| 5,149,092 | A | 9/1992 | Parsons | |
| 5,152,627 | A * | 10/1992 | Arnold | B62D 1/185 403/109.3 |
| 5,167,805 | A * | 12/1992 | Theiss | E04H 4/1609 15/1.7 |
| 5,387,048 | A | 2/1995 | Kuo | |
| 5,590,974 | A | 1/1997 | Yang | |
| 5,667,329 | A | 9/1997 | Yoder, Jr. | |
| 6,059,531 | A * | 5/2000 | Tai | F04D 29/34 403/326 |
| 6,263,895 | B1 * | 7/2001 | Bang | E04H 15/44 135/138 |
| 6,343,890 | B1 | 2/2002 | Benson | |
| 6,824,180 | B2 * | 11/2004 | Tomchak | A01B 1/22 294/57 |
| 7,730,930 | B2 * | 6/2010 | Malausa | B60J 1/2019 160/310 |
| 8,974,261 | B2 * | 3/2015 | Kicker | B63H 16/04 440/101 |
| 2003/0215283 | A1 | 11/2003 | Hsieh | |
| 2004/0145198 | A1 | 7/2004 | Tomchak | |
| 2005/0019138 | A1 | 1/2005 | Stockler | |
| 2005/0097691 | A1 | 5/2005 | Tsuchiya et al. | |
| 2006/0002759 | A1 * | 1/2006 | Blackman | F16B 7/044 403/109.3 |
| 2006/0046899 | A1 * | 3/2006 | Wang | A63B 71/023 482/27 |
| 2008/0000596 | A1 * | 1/2008 | Malausa | B60J 1/2019 160/291 |
| 2013/0266364 | A1 | 10/2013 | John | |
| 2013/0333322 | A1 | 12/2013 | Stein | |
| 2014/0263031 | A1 * | 9/2014 | Lawson | B25G 3/26 210/470 |

FOREIGN PATENT DOCUMENTS

| | | | | |
|---|---|---|---|---|
| DE | 2254953 | A1 * | 5/1974 | ............. F16B 7/105 |
| DE | 2254953 | A1 | 5/1974 | |
| DE | 3713409 | A1 * | 11/1988 | ............. A45B 11/00 |
| DE | 9105664 | U1 * | 7/1991 | ......... A47B 47/0008 |
| DE | 4443198 | A1 * | 6/1996 | ........... E04B 2/7438 |
| DE | 4443198 | A1 | 6/1996 | |
| DE | 29917122 | U1 * | 3/2000 | ............. A45B 9/00 |
| FR | 462618 | A * | 1/1914 | ............. F16B 7/105 |
| FR | 744194 | A * | 4/1933 | ............. F16B 7/105 |
| FR | 2676513 | B1 * | 7/1994 | ........... A47B 57/485 |
| FR | 2916495 | B1 * | 9/2009 | ............. F16B 7/042 |
| GB | 191406781 | A * | 3/1915 | ............. F16B 7/042 |
| GB | 1210093 | A | 10/1970 | |
| GB | 1210093 | A * | 10/1970 | ............. D06F 53/04 |
| GB | 2409009 | A * | 6/2005 | ............. F16B 7/042 |
| WO | WO-2006117419 | A1 * | 11/2006 | ............. E06B 9/76 |
| WO | WO-2014170837 | A1 * | 10/2014 | ............. A47L 13/20 |

* cited by examiner

SPRING FOR CONNECTING A PIPE TO A CONNECTOR

CROSS-REFERENCE TO RELATED APPLICATIONS

This application is a National Phase of PCT Patent Application No. PCT/IL2016/050097 having International filing date of Jan. 28, 2016, which claims the benefit of priority of U.S. Provisional Patent Application No. 62/109,202, filed on Jan. 29, 2015 and entitled "A Spring for Connecting a Pipe to a Connector." The content of both applications are incorporated herein by reference in their entirety.

TECHNICAL FIELD

The present disclosure relates to pipes in general, and to an apparatus and method for a durable pipe connector, in particular.

BACKGROUND

Many applications require multiple pipes to be connected, whether in continuation to one another to obtain longer stretches, at an angle to one another, or a combination thereof. In some applications two pipes may be connected to each other at each connection, while in other a multiplicity of pipes may be connected at an area. In further applications, a single pipe may be connected, for example when connecting a water pipe to a wall.

Such connected pipes are used in a multiplicity of applications, such as plumbing, protecting electrical cables, erecting fixed or temporary structures such as tent skeletons, children play structures, or the like.

In some connection techniques, each pipe connects directly to another pipe, for example by providing pipes of varying diameters such that an end of one pipe may be inserted into an end of another pipe. In other techniques, connectors are provided such that each pipe connects to the connector, and if two or more pipes are to connect, their connection is formed by each pipe connecting to the connector.

In those techniques that include a connector, a significant challenge is creating an easy to assemble and easy to remove connection, which is also strong enough and does not open unintentionally.

In some implementations, the connector has one or more protruding members such as protruding rods each of which may be inserted into a pipe when connecting the pipe to the connector. The protruding member may comprise one or more leaf springs each having a button-like piece thereon, wherein one end of the leaf spring is connected to the connector. The pipe has one or more holes or openings in locations corresponding to the location of the button-like pieces on the leaf springs, such that when the protruding part is inserted into the pipe, the button-like pieces pop out of the openings. When the pipe is to be removed, a user has to push the button-like pieces while pulling the pipe from the connector to release it.

However, connecting and releasing the pipe from the connector implies pushing the button and thus activating force on the connection of the leaf spring to the connector. Repeatedly connecting and releasing the pipe may therefore lead to breakage of the leaf spring at the area where it is attached to the connector, such that the pipe can unintentionally disconnect from the connector.

There is thus a need in the art for a durable system for connecting a pipe to a connector.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a spring for connecting a pipe to a rod, the spring comprising: a flat tab attached to a rod, wherein the flat tab is aligned with a first face of the rod; an unattached tab aligned with a second face of the rod that is opposite to the first face; a substantially diagonal bridge connecting the flat tab and the unattached tab, wherein the angle between the attached tab and the diagonal bridge is greater than 90; and a button located on the flat tab, wherein the button protrudes from the distal end of the rod when the spring is normally open, and wherein the button is configured to engage with a corresponding hole in a pipe.

In some embodiments, the unattached tab comprises an outwardly convex end and an uplifted tip configured to press against the inner wall of the pipe, wherein the outwardly convex end protrudes from the rod when the spring is normally open, and wherein the spring is configured to be compressed such that the button does not protrude from the distal end of the rod and the outwardly convex end does not protrude from the rod.

In some embodiments, the attached flat tab is attached to a distal portion of the distal end of the rod.

In some embodiments, the attached flat tab is attached to a proximal portion of the distal end of the rod.

In some embodiments, the button has a gradient in at least a proximal or a distal face.

In some embodiments, the unattached tab is a flat tab that is aligned with the rod.

In some embodiments, the spring further comprises a second protruding button located on the unattached tab, wherein the second protruding button is configured to engage with a second corresponding hole in the pipe.

In some embodiments, the second button has a gradient in at least a proximal or a distal face.

In some embodiments, the attached flat tab and the unattached flat tab are parallel to each other.

There is provided, in accordance with an embodiment, an S-shaped spring connector for attaching a pipe to a rod, the S-shaped spring connector comprising: an S-shaped leaf spring comprising: an attached flat tab disposed with a protruding button, wherein the button is configured to engage with a corresponding hole in a pipe, an unattached tab disposed with a convex end, and a substantially diagonal bridge connecting the attached flat tab to the unattached tab, wherein the angle between the attached tab and the diagonal bridge is greater than 90°; a rod comprising a distally-disposed elongated cavity, wherein the attached tab is attached to the rod such that the S-shaped leaf spring is enclosed in the elongated cavity and the attached flat tab is aligned with a first face of the rod and the unattached tab is aligned with a second face of the rod that is opposite to the first face, wherein the protruding button is exposed at the first face of the cavity and the convex end is disposed at the second face of the cavity, and wherein when the S-shaped leaf spring is in a normally open configuration, the button and the convex end protrude outwards from the distal end of the rod.

In addition to the exemplary aspects and embodiments described above, further aspects and embodiments will become apparent by reference to the figures and by study of the following detailed description.

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
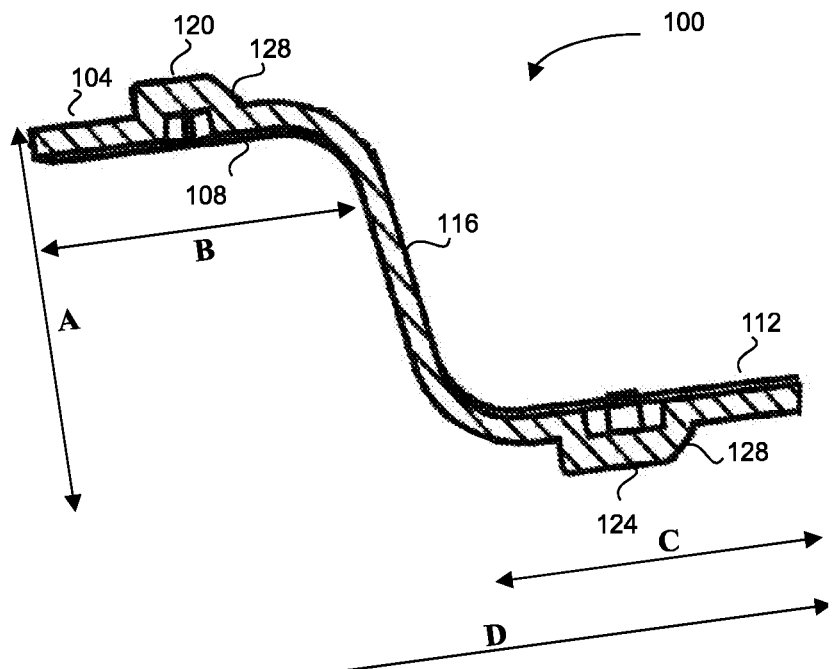
FIG. 1 is a schematic side view of a leaf spring, in accordance with some exemplary embodiments of the disclosure.

The disclosure relates to an advantageous leaf spring, which may be included in a system for connecting a pipe to a connector such that the connection is durable and may endure an unlimited number of connections and releases. In the disclosure below the terms "pipe" and "tube" are used interchangeably and may relate to an elongated hollow structure having open ends, and having any required cross section.

In some embodiments, the connector comprises one or more protruding rods, each of which may be used for connecting one pipe to the connector. Each such protruding rod may have thereon a leaf spring connected at one end to the protruding rod. The leaf-spring is substantially S-shaped.

In one embodiment, the leaf spring may comprise two tabs each aligned with an opposite face of the protruding rod, or touching opposing internal faces of the pipe into which the protruding rod is inserted, where at least one of the tabs is flat, and the tabs are connected by a substantially diagonal bridge. In one embodiment, both tabs are flat and parallel to each other. At least the tab near the connection to the protruding rod, and optionally both tabs, may have a button for engaging with corresponding holes provided on the pipe to be connected, to lock the spring, and therefore the joint, inside the pipe. When the spring is normally open the button protrudes from the rod.

One of the tabs, e.g. the distal tab which is inserted farther into the pipe, may be attached to the protruding rod, while the other tab is not connected to the rod. Alternatively, the proximal tab may be attached to the protruding rod and the distal tab may be unconnected to the rod. However, as mentioned above, the two tabs are aligned with opposing faces of the protruding rod, and therefore are aligned with or at least touch opposing sides or areas of the inner surface of a pipe into which the protruding rod is inserted. It will be appreciated that although the term opposing faces may relate to a pipe or rod having rectangular cross section, it may also relate to areas around the two ends of a radius of a round pipe or rod, or any other two areas far from each other, depending on the cross section of the rod or pipe.

Thus, when stress is applied at the button located on the tab closer to where the leaf spring connects to the protruding rod in order to release the spring, the stress is transferred to the diagonal bridge and therefrom to the inner surface of the pipe upon which it leans, thus preventing breakage even under extreme stress. Once compressed, the button or buttons disengage from the holes of the pipe, unlocking the joint.

While connecting a pipe to the connector, the protruding rod is inserted into the tube at the distal end until the tube presses on both tabs and compresses the spring. At the beginning of the insertion, the distally positioned tab is slightly depressed into the rod and the proximally positioned tab is slightly expressed from the rod. When insertion continues, the proximal positioned tab is slightly depressed as well. This positions the button on the attached tab for engaging with a hole of the tube, releasing the spring and locking the rod inside the tube.

In order to release the pipe, the button is pressed, thus compressing the spring, without actuating force on the connection of the leaf spring to the protruding rod. The freely moving unattached tab thus provides the spring with flexibility for easy locking and unlocking. However, the motion at the attached tab is constrained by the tube and the pressure applied to unlock the spring is transferred to the diagonal bridge and to the pipe surface, thus alleviating stress that could break the attached tab from the rod.

Once compressed, the button disengages from the hole of the pipe, unlocking the spring, such that the rod can slip out of the tube.

In one embodiment, each tab is disposed with a button, and inserting the rod inside the pipe engages each button of each tab with oppositely positioned holes of the pipe. Releasing the pipe is similar to that described above with the noted exception that both buttons are to be pressed simultaneously to compress the spring and disengage both buttons from the holes of the pipe, unlocking the spring.

Referring now to FIG. 1 showing a schematic perspective view of the leaf spring. The leaf spring, generally referenced 100, connects at distal end 104 to a protruding rod of the connector. The leaf spring comprises flat distal tab 108 and flat proximal tab 112, connected by substantially diagonal bridge 116, where the angle between either of tabs 108 or 112 and diagonal bridge 116 is obtuse, or greater than 90°. The obtuse angle may range from 95° to 115°, or from 95° to 120°, or from 95° to 130°, or from 95° to 140°. In one embodiment, one of distal tab 108 or proximal tab 112 may is disposed with a protruding button 124. In another embodiment, both of distal tab 108 and proximal tab 112 are disposed with protruding buttons 124 and 120.

In order to demonstrate proportion requirements, the height (or diameter, or similar measure, depending on the cross section) of the protruding rod is indicated A. Depending on the diameter or another dimension of the cross section of the pipe it is required to connect, A may vary, for example, between 5 mm and 500 mm. It will be appreciated that length B of distal tab 108 and length C of proximal tab 112 may be between a fraction of A and a multiplicity of A, for example between 0.1*A and 3*A. The length of projection D of the leaf spring has to be larger than B+C, and depends on the angles between bridge 116 and tabs 108 and 112. Each angle may be anywhere between 90° and 180°, for example, between 145° and 160°.

It will be appreciated that each of buttons 120 or 124, instead of having a step-like cross-section, may comprise a gradient 128 at its distal and/or proximal side, to enable easy connection or release.

Figure 2:
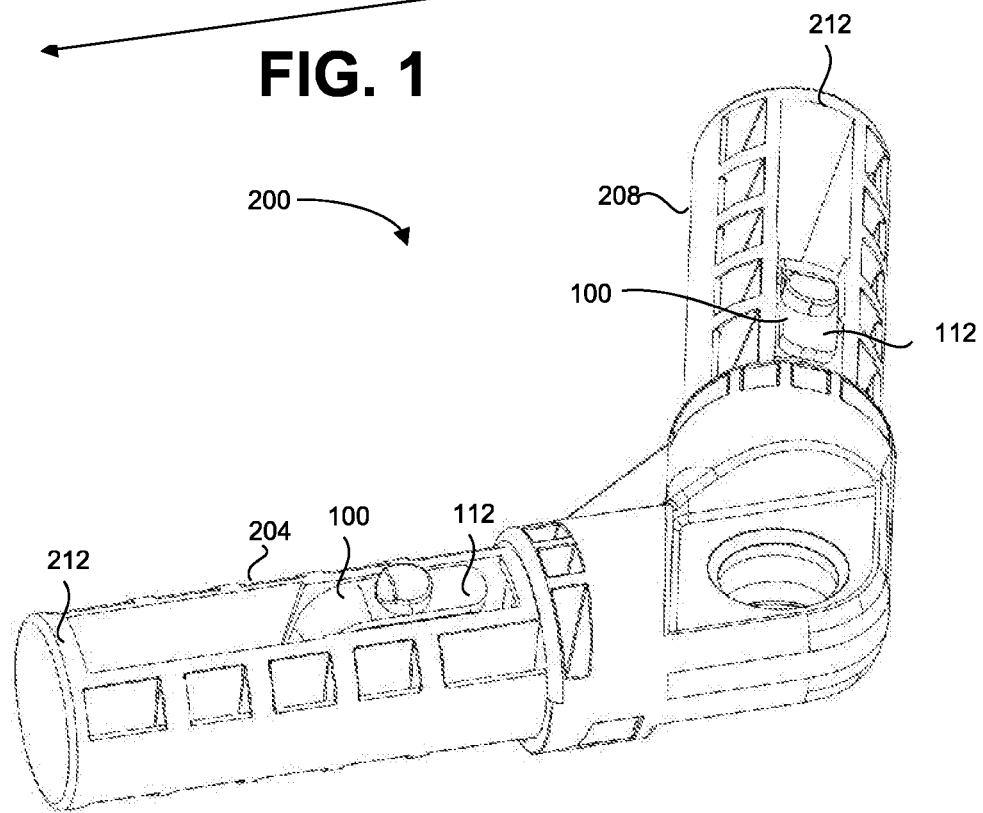
FIG. 2 is a schematic cross section of a connector with a leaf spring, in accordance with some exemplary embodiments of the disclosure.

Referring now to FIG. 2, showing a schematic perspective view of a connector with a leaf spring. The connector, generally referenced 200 comprises protruding rods 204 and 208, each of which comprises leaf spring 100.

It can be seen that leaf spring 100 is connected to connector 200 at the connector distal end, such that proximal tab 112 at the other end of leaf spring 100 is unattached and is aligned with side 212 of protruding rods 204 and 208. Alternatively, leaf spring 100 may be connected to connector 200 at the connector proximal end, such that distal tab 112 at the other end of leaf spring 100 is unattached and is aligned with side 212 of protruding rods 204 and 208.

Figure 3:
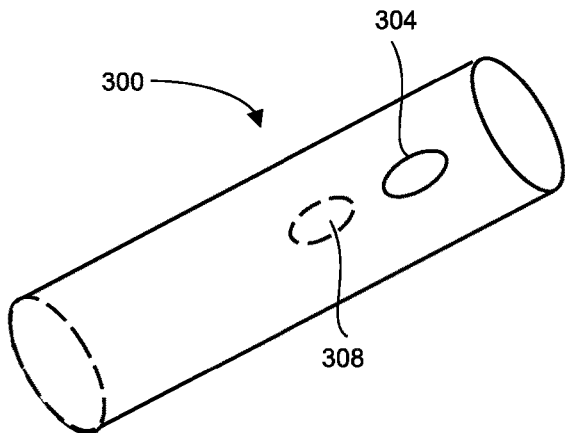
FIG. 3 is a side view of a pipe to be connected using a connector with a leaf spring, in accordance with some exemplary embodiments of the disclosure.

Referring now to FIG. 3, showing a perspective view of a pipe 300 to be connected using a connector with a leaf spring. The pipe comprises two holes 304 and 308 on opposite sides of pipe 300, into which protruding buttons 120 and 124 pop when the pipe is connected.

It will be appreciated that the disclosure may be used with a pipe having any required cross section, such as a circle, a square, a rectangle, a triangle, or any arbitrary cross section.

Figure 4:
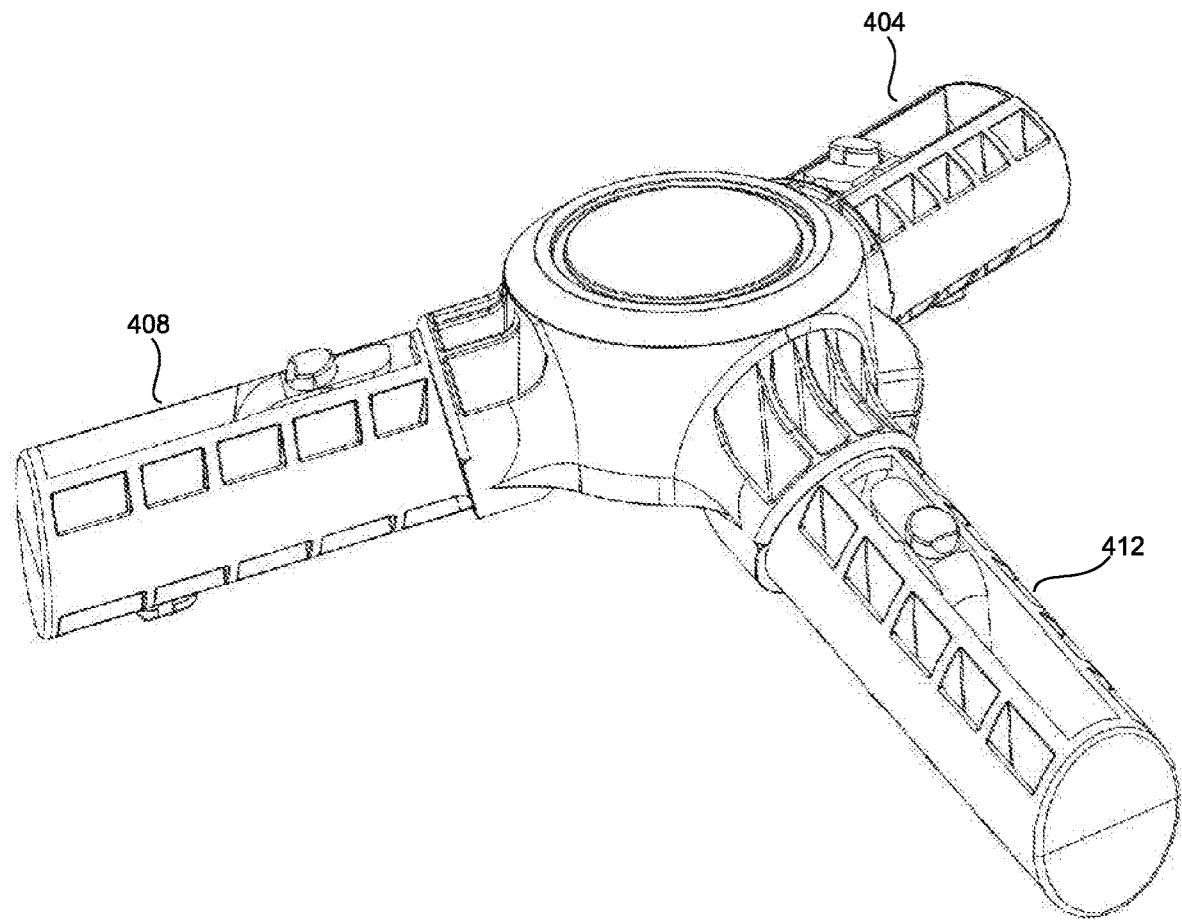
FIG. 4 is a top view of a 3-way connector with leaf springs, in accordance with some exemplary embodiments of the disclosure.

Referring now to FIG. 4 showing a perspective view of a 3-way connector with three protruding rods 404, 408 and 412, each having a leaf spring, wherein the unattached sides of the spring leaves are shown.

Figure 5A:
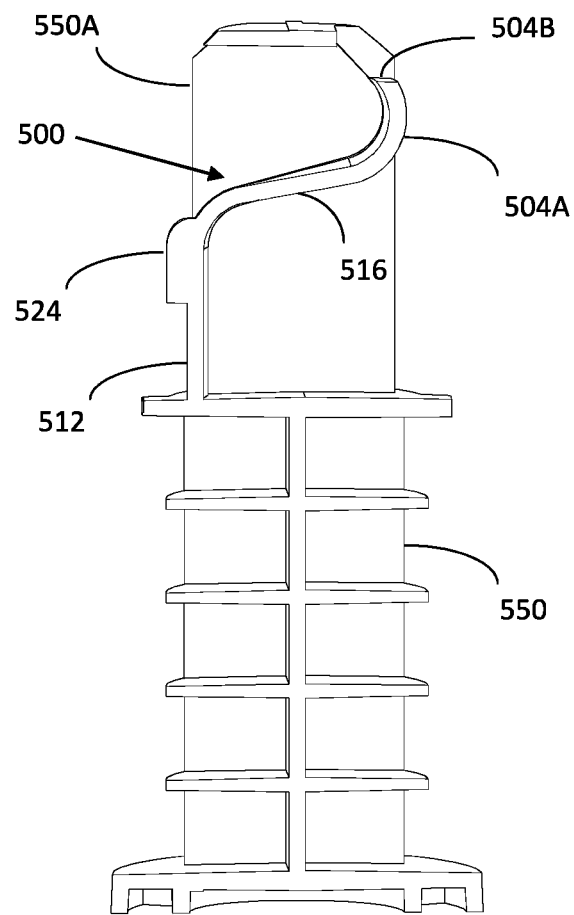
FIGS. 5A-E illustrate multiple views of a leaf spring in accordance with another embodiment.
Figure 5B:
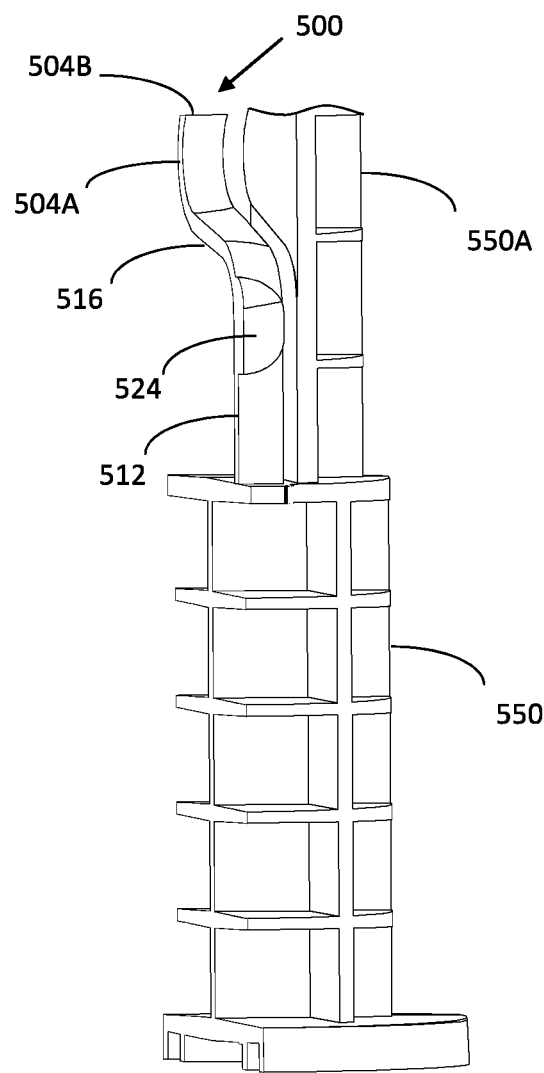

Reference is now made to FIGS. 5A-E which illustrate multiple views of a leaf spring 500 in accordance with another embodiment. Referring to FIGS. 5A-5B, a side view and a perspective view of leaf spring 500 are shown. Leaf spring 500 may be substantially S-shaped, having a diagonal bridge 516 connecting a flat tab 512 to an unattached tab comprising an outwardly convex end 504A with an uplifted tip 504B, where the angle between flat tab 512 and diagonal bridge 516 is obtuse, or greater than 90°. The obtuse angle may range from 95° to 115°, or from 95° to 120°, or from 95° to 130°, or from 95° to 140°.

A protruding button 524 may be disposed with flat tab 512. Button 524 may protrude by a distance E (shown in FIG. 5C) from flat tab 512, and may have a gradient that tapers in the direction of diagonal bridge 516, similar to button 124 above allowing for inserting into pipe 300. Button 524 may be configured to engage with one of holes 304 or 308 in pipe 300 above.

Leaf spring 500 may be substantially similar to leaf spring 100 with the notable difference that leaf spring 500 has only a single protruding button 524 at one end, with convex end 504A and uplifted tip 504B replacing the second protruding button 120 of leaf spring 100.

Figure 5C:
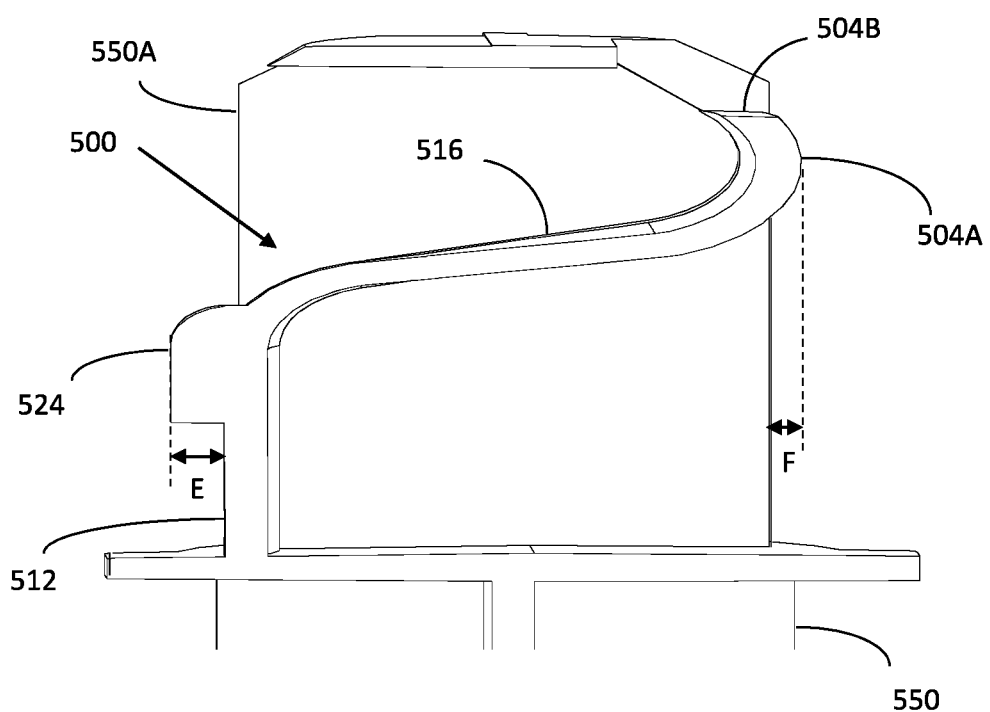

Leaf spring 500 may be disposed at the distal end 550A of a connector rod 550, which is shown in FIGS. 5A-5C longitudinally cross-sectioned for the sake of visibility. In the configuration shown in FIGS. 5A-5E, flat tab 512 is attached to a proximal portion of the distal end 550A of rod 550, thereby disposing outwardly convex end 504A and uplifted tip 504B distally. However, in an alternate configuration (not shown), flat tab 512 may be attached at the distal portion of the distal end 550A of rod 550, thereby disposing outwardly convex end 504A and uplifted tip 504B proximally, similar to the attachment of spring 100 to rod 204 and 208 shown in FIGS. 2 and 4. Flat tab 512 is aligned with one face of rod 550 and the unattached tab comprising convex end 504A and uplifted tip 504B is aligned with the opposite face of rod 550. When leaf spring 500 is normally open, button 524 and convex end 504A protrude from opposite faces of the distal end 550A of rod 550.

Referring to FIG. 5C, an enlarged view of a side view of leaf spring 500 is shown. Leaf spring 500 may be normally open. In its normally open configuration, convex end 504A may protrude slightly, or bulge outwards from distal end 550A of rod 550 by a distance F. Similarly, button 524 may protrude outwards from distal end 550A of rod 550 by distance E. Thus the width of leaf spring 500 in the normally open position may exceed the inner diameter of pipe 300 by an amount corresponding to the height E of button 524 and the outwards bulge F of convex end 504A.

For example, E and/or F may range from 0.5 mm to 5 mm, or from 0.75 mm to 4 mm, or from 1 mm to 3 mm, or from 1.5 mm to 2.5 mm. The length of connected tab 512 may range from 5 mm to 200 mm. The length of button 524 may range from 1 mm to 10 mm. The length of bridge 516 may range from 10 mm to 40 mm. The length of convex end 504A and uplifted tip 504B may range from 5 mm to 200 mm. The distance between uplifted tip 504B and the outer peak of convex end 504A may range from 0.1 mm and 2 mm.

Pipe 300 may have an inner diameter corresponding to the distal end 550A of rod 550. Accordingly, when inserting the distal end 550A of rod 550 into pipe 300, pipe 300 may press convex end 504A and protruding button 524 inwards, thereby compressing leaf spring 500 by a distance of approximately E+F corresponding to the inner diameter of pipe 300, and allowing distal end 550A to enter pipe 300. The obtuse angle between flat tab 512 and diagonal bridge 516 may increase slightly, causing leaf spring 500 to flatten, and convex end 504A to slide forward. When rod 550 is inserted sufficiently to lock within pipe 300, button 524 may engage with one of holes 304 or 308 and pop out of pipe 300, partially releasing spring 500 by a distance of approximately E, and locking rod 550 inside pipe 300. It may be noted that when rod 550 is thus locked inside pipe 300, leaf spring 500 may still be partially compressed by an amount corresponding to distance F, and convex end 504A may exert pressure against the inner wall of pipe 300. In this embodiment, pipe 300 may be configured with only one of holes 304 or 308, allowing convex end 504A to press against the inner wall of pipe 300, leaving spring 500 partially compressed within pipe 300.

Disengaging rod 550 from pipe 300 may require pressing only the single button 524 to release it from the hole. The stress exerted on button 524 may be transferred to diagonal bridge 516 and therefrom to the inner surface of the pipe 300 upon which it leans, thus preventing flat tab 512 from breaking off rod 550 even under extreme stress. Once compressed, button 524 may disengage from the hole of pipe 300, unlocking rod 550 from pipe 300 allowing it to slip out.

Figure 5D:
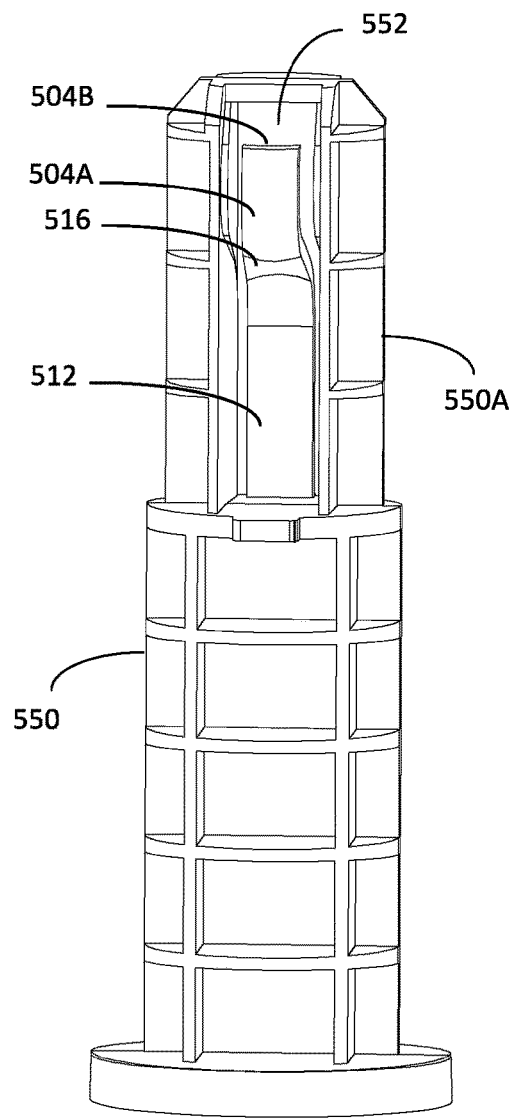
Figure 5E:
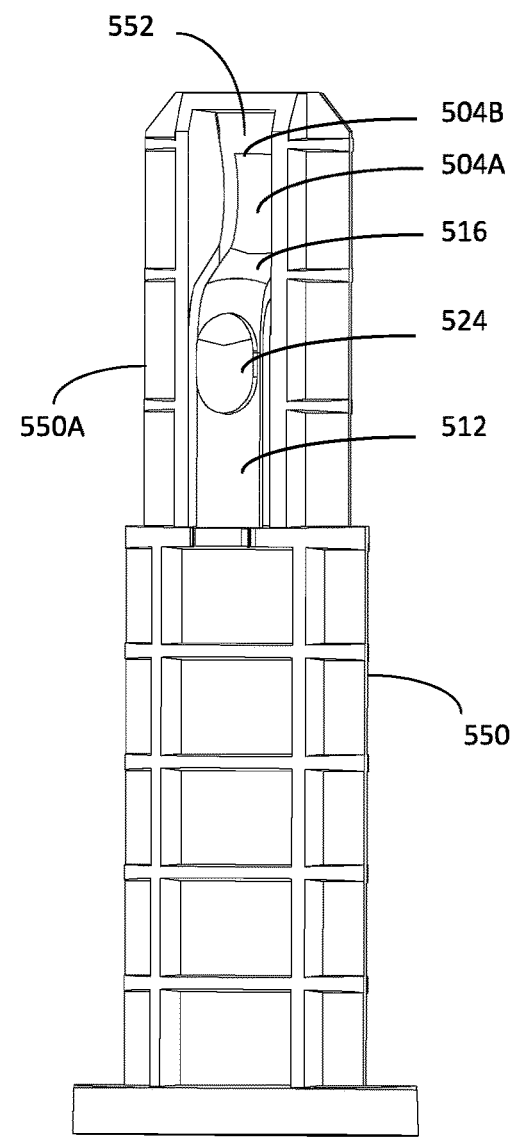

Reference is now made to FIGS. 5D-5E which show back and front views of leaf spring 500, respectively, attached to distal portion 550A of rod 550 and enclosed within a distally disposed elongated cavity 552 of distal portion 550A of rod 550. Flat tab 512 is aligned with the front face of distal portion 550A (FIG. 5E) and the unattached tab, comprising convex end 504A and tip 504B are aligned with the rear face of distal portion 550A (FIG. 5D). Distal portion 550A allows only the rear face (FIG. 5D) and front face (FIG. 5E) of spring 500 to be exposed, thereby exposing convex end 504A and button 524, while protecting tip 504B from breakage. Cavity 552 may provide sufficient longitudinal clearance to allow spring 500 to lengthen within cavity 552 when compressed.

The inner diameter of pipe 300 may be sized according to distal rod portion 550A, button 524 and convex end 504A may extend out from rod portion 550A by amounts E and F, respectively. Thus, exposed convex end 504A and exposed button 524 may pose a small barrier, requiring spring 500 to be compressed when inserting portion 550A into pipe 300. The compression requirements may be sufficiently small to allow for easy, manual insertion of portion 550A into pipe 300. For example, button 524 may be manually compressed while resistance from the inner wall of pipe 300 may be sufficient to compress convex end 504A to allow inserting portion 550A into pipe 300. Alternatively, the resistance from the inner wall of pipe 300 may be sufficient to compress both button 524 and convex end 504A to allow inserting portion 550A into pipe 300.

Leaf spring 100 or 500 may be manufactured of the same material as the protruding rod, or form a material that may be connected to the material of the rod. Such material may be selected from, but is not limited to any of the following: ABS, ABS with Glass Fiber, ABS/PC, ABS/PC with Glass Fiber, Acetal, Acetal with Glass Fiber, Acrylic (PMMA), Acrylic (PMMA) with Glass Fiber, ETPU, ETPU with Glass Fiber, HDPE, HDPE with Glass Fiber, LCP, LCP with Glass Fiber, LDPE, LDPE with Glass Fiber, LLDPE, LLDPE with Glass Fiber, Magnesium, MIM Nickel Steel, MIM Stainless Steel, Nylon, Nylon with Glass Fiber, PBT, PBT with Glass Fiber, PC, PC with Glass Fiber, PC/PBT, PC/PBT with Glass Fiber, PEEK, PEEK with Glass Fiber, PEI, PEI with Glass Fiber, PP (Polypropylene), PP with Glass Fiber, PPS, PPS with Glass Fiber, PPSU, PPSU with Glass Fiber, Aluminum, Copper, Iron, Nickel, Platinum, Silver, Tin, Zinc, Brass, Bronze, Steel, Chromoly, Stainless Steel, Tool Steel, Titanium, Any Combination of Alloy, SB, SB with Glass Fiber, Silicone, Silicone with Glass Fiber, TPE, TPE with Glass Fiber, TPU-Polyester, TPU-Polyester with Glass Fiber, TPV, TPV with Glass Fiber, or any other similar material.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A spring for a connector having at least one rod for connecting to a pipe, the spring comprising:
    a first end integrally attached to said rod, said rod having an elongated cavity accommodating at least a portion of the spring, and comprising a proximal flat tab that is aligned with a first face of the rod;
    a second unattached end comprising a distal tab aligned with a second face of the rod that is opposite to the first face;
    a diagonal bridge connecting the proximal tab and the distal tab, wherein the angle between the proximal tab and the diagonal bridge is greater than 90°;
    a first button located at least on the proximal flat tab, wherein the button protrudes from the distal end of the rod when the spring is normally open, and wherein the button is configured to engage with a corresponding hole in a pipe; and
    wherein the spring is configured to lengthen within the elongated cavity when compressed.

2. The spring of claim 1, wherein the distal tab at the unattached end comprises an outwardly convex end and an uplifted tip configured to press against the inner wall of the pipe, wherein the outwardly convex end protrudes from the rod when the spring is normally open.

3. The spring of claim 1, wherein the integrally attached flat tab is attached to a distal portion of the distal end of the rod, the tab and rod forming a unitary connector.

4. The spring of claim 1, wherein the integrally attached flat tab is attached to a proximal portion of the distal end of the rod, the tab and rod forming a unitary connector.

5. The spring of claim 1, wherein the button has a gradient in at least a proximal or a distal face.

6. The spring of claim 1, wherein the spring is a leaf spring and further comprising a second protruding button located on the distal tab, wherein the first button and the second button are located on opposite faces of the spring.

7. The spring of claim 6, wherein the second button has a gradient in at least a proximal or a distal face.

8. The spring of claim 1, wherein the attached flat tab and the unattached flat tab are disposed at different axial locations along a longitudinal axis of the rod.

9. The spring of claim 1, wherein the proximal tab and the distal tab are disposed on opposite faces of the spring such that depression of one tab into the rod brings about protrusion of the other tab from the rod.

10. The spring of claim 1, wherein said spring and said rod are manufactured of the same material and form a unitary connector.

11. The spring of claim 10, wherein said spring is a leaf spring that axially protrudes from said rod.

12. A connector having at least one rod for attaching to a pipe, comprising:
    an S-shaped leaf spring comprising:
        an attached flat tab disposed with a protruding button, wherein the button is configured to engage with a corresponding hole in a pipe,
        an unattached tab disposed with a convex end, and
        a diagonal bridge connecting the attached flat tab to the unattached tab, wherein the angle between the attached tab and the diagonal bridge is greater than 90°;
    a rod comprising a distally disposed elongated cavity, wherein the attached tab is integrally attached to and in continuum with the rod such that the S-shaped leaf spring is enclosed in the elongated cavity and configured to lengthen within the elongated cavity when compressed;

wherein the attached flat tab is aligned with a first face of the rod and the unattached tab is aligned with a second face of the rod that is opposite to the first face, wherein the protruding button is exposed at the first face of the cavity and the convex end is disposed at the second face of the cavity; and wherein when the S-shaped leaf spring is in a normally open configuration, the button and the convex end protrude outwards from the distal end of the rod.

* * * * *